US009358312B2

(12) United States Patent
Scheuren et al.

(10) Patent No.: US 9,358,312 B2
(45) Date of Patent: Jun. 7, 2016

(54) METHOD AND APPARATUS FOR THE STERILIZATION OF CONTAINERS WITH CLEANING OF A RADIATION OUTLET WINDOW

(71) Applicant: KRONES AG, Neutraubling (DE)

(72) Inventors: Hans Scheuren, Bad Kreuznach (DE); Josef Knott, Schierling (DE)

(73) Assignee: KRONES AG (DE)

( * ) Notice: Subject to any disclaimer, the term of this patent is extended or adjusted under 35 U.S.C. 154(b) by 0 days.

(21) Appl. No.: 14/476,385

(22) Filed: Sep. 3, 2014

(65) Prior Publication Data

US 2015/0064062 A1 Mar. 5, 2015

(30) Foreign Application Priority Data

Sep. 3, 2013 (DE) .......................... 10 2013 109 584

(51) Int. Cl.
*A61L 2/08* (2006.01)
*H01J 33/04* (2006.01)

(52) U.S. Cl.
CPC ............. *A61L 2/087* (2013.01); *A61L 2202/23* (2013.01); *H01J 33/04* (2013.01)

(58) Field of Classification Search
CPC ........................................................ A61L 2/087
USPC ........................................ 422/22; 250/453.11
See application file for complete search history.

(56) References Cited

U.S. PATENT DOCUMENTS

| 8,821,788 | B2 | 9/2014 | Krueger et al. ............... 422/22 |
| 2009/0045350 | A1* | 2/2009 | Humele ................. A61L 2/087 |
| | | | 250/455.11 |
| 2011/0076187 | A1 | 3/2011 | Foell et al. ................... 422/22 |
| 2011/0262866 | A1 | 10/2011 | Nakayama et al. ............ 430/311 |
| 2013/0216430 | A1 | 8/2013 | Knott et al. .................... 422/22 |

FOREIGN PATENT DOCUMENTS

| DE | 10 2008 025 868 | 12/2009 | ............. B65B 55/05 |
| DE | 202012103519 | 10/2012 | ................ A61L 2/08 |
| DE | 10 2011 052 862 | 2/2013 | ................ A61L 2/08 |
| EP | 2161202 | 3/2010 | ................ A61L 2/08 |
| EP | 2559444 | 2/2013 | ................ A61L 2/08 |
| JP | 2003337199 | 11/2003 | ............... G21K 5/00 |
| JP | 2011-243949 | 12/2011 | ........... H01L 21/027 |

(Continued)

OTHER PUBLICATIONS

Extended European Search Report (no translation) issued in related application No. 14183361.6, dated Jan. 26, 2015 (5 pgs).

(Continued)

*Primary Examiner* — Sean E Conley
(74) *Attorney, Agent, or Firm* — Hayes Soloway P.C.

(57) ABSTRACT

A method of operating an apparatus for the sterilization of plastics material containers is provided, wherein charge carriers are generated in a working operation and are conveyed through a guide chamber and emerge from this guide chamber by way of an outlet window bounding this guide chamber and wherein the outlet window is introduced into the plastics material containers at least in part through an aperture of the aforesaid plastics material containers during the sterilization of the plastics material containers. The outlet window is acted upon with a flowable cleaning medium in a cleaning operation of the apparatus.

19 Claims, 2 Drawing Sheets

(56) References Cited

FOREIGN PATENT DOCUMENTS

| WO | WO2009144114 | 12/2009 | ................ | A61L 2/08 |
| WO | WO2014095937 | 6/2014 | ................ | A61L 2/08 |

OTHER PUBLICATIONS

German Search Report issued in corresponding German Patent Appln. No. 10 2013 109 584.4 dated Mar. 28, 2014 (5 pgs).

* cited by examiner

METHOD AND APPARATUS FOR THE STERILIZATION OF CONTAINERS WITH CLEANING OF A RADIATION OUTLET WINDOW

BACKGROUND OF THE INVENTION

The present invention relates to a method of operating an apparatus for the sterilization of containers, and in particular of plastics material containers, as well as to a corresponding apparatus for the sterilization of plastics material containers. Methods and apparatus of this type have long been known from the prior art. Whereas it was usual in the past to carry out a sterilization of this type by the use of chemical substances, such as for example hydrogen peroxide or peracetic acid, attempts have been made in recent years to reduce the use of chemicals of this type. Methods are therefore also known from the prior art in which plastics material containers are sterilized by irradiation, for example by irradiation with X-ray or UV radiation, or recently also by irradiation with charge carriers, such as in particular electrons.

A difficulty in this case is, in particular, the internal sterilization of containers, i.e. the sterilization of the inner wall of plastics material containers of this type. To this end, it is known for radiation fingers to be introduced into the interior of plastics material containers of this type and for the inner wall of the plastics material containers to be acted upon with the electrons there.

For this purpose, apparatus of this type have electron generation devices or charge-carrier generation devices and usually also acceleration devices which accelerate these charge carriers—in particular inside a vacuum chamber—in the direction of an outlet window. The charge carriers in turn can emerge through this outlet window which may be for example a titanium window. In prolonged operation of radiation apparatus of this type, however, it was found that the radiation apparatus are subjected over time to drops in performance.

The object of the present invention is therefore to provide possibilities which maintain the performance of radiation fingers of this type even over prolonged periods of time.

SUMMARY OF THE INVENTION

In the case of a method according to the invention for operating an apparatus for the sterilization of plastics material containers, charge carriers are generated in a working operation and are conveyed through a guide chamber. In addition, these charge carriers will emerge from this guide chamber by way of an outlet window bounding this guide chamber and the outlet window is introduced into the plastics material containers at least in part and preferably also at least for a time through an aperture of the aforesaid plastics material containers during the sterilization of the plastics material containers.

According to the invention the outlet window is acted upon with a flowable cleaning medium or is subjected to it respectively in a cleaning operation of the apparatus. It has been possible to establish that one reason for the drop in performance of radiation devices of this type is that in prolonged operation the radiation devices have an increasing deposit of dirt. The contamination is explained by interactions of the charge carriers emerging from the outlet window with the air of the environment. The reaction products settle accordingly on the outlet window. These reaction products can be silicate compounds for example.

The invention is therefore based upon the concept of carrying out a cleaning of this outlet window at, in particular, periodic intervals. This cleaning preferably takes place at times other than working operation. It is therefore preferable for the cleaning of the outlet windows to be carried outside working operation. The cleaning in this case can be carried out manually, partly automatically or even fully automatically.

It is preferable for the aforesaid outlet windows to be moved into containers for the sterilization. In particular the plastics material containers are plastics material pre-forms which are preferably used for the production of plastic bottles. It is advantageous for the apparatus to have a rod-like body which is capable of being introduced into the interior of the plastics material pre-forms. It is advantageous in this case for the aforesaid guide chamber to be formed at least in part inside this rod-like body.

It is advantageous for the aforesaid outlet window to be arranged in an end portion of this radiation finger.

In the case of a further advantageous embodiment a drive device is provided for moving the aforesaid outlet windows into a container with a cleaning medium, in particular within the framework of the cleaning operation.

It is advantageous for the cleaning medium to be a liquid cleaning medium. The cleaning medium is preferably present inside the plastics material container/plastics material pre-form (in particular during the cleaning procedure). This means that a plastics material container, and in particular a plastics material container of the type of those plastics material containers which are to be sterilized, is used in the cleaning procedure as a receiving container for receiving the cleaning medium.

In addition, the same drive device may be involved which also produces the relative movement between the containers and the outlet window during the working operation.

In the case of a further preferred method the generation of the charge carriers is carried out outside the plastics material pre-form during the sterilization operation. In this way, the charge carriers are preferably first generated, are preferably accelerated by means of an acceleration device, and then emerge (inside the plastics material container) through the outlet window. The emergence of the charge carriers is carried out in particular before the dipping of the radiation finger or the rod-like body respectively in the plastics material container. As a result of this it is possible for the upper aperture region or the entire thread region respectively of the plastics material pre-form to be sterilized.

In the case of a further preferred method the outlet window is cooled at least for a time by being acted upon with a gaseous medium during the working operation.

In the case of a further advantageous method at least one element of a device for cooling the outlet window is removed from the guide chamber before the beginning of the cleaning operation. This further element can be for example a tube which surrounds this guide chamber. It is advantageous for an air gap, through which cooling air is conveyed, to be formed at least locally in a peripheral direction of this guide chamber. It is advantageous for this air gap to be formed between the guide chamber, in particular an outer wall of the guide chamber, and the aforesaid tube.

In addition, it would also be possible for a flowable cleaning medium to be supplied by way of the cooling-air supply described here. In this case it is preferable for a gaseous cleaning medium to be supplied by way of the cooling-air supply. In addition, it would be possible for a cleaning to be carried out both with a gaseous cleaning medium and with a liquid cleaning medium. In this case these cleaning media could be supplied in a manner staggered in time or even (at least in part) at the same time. In general, the flowable cleaning medium can thus also be a gaseous cleaning medium.

In other words, in a first step the aforesaid cooling tube, i.e. the further element, can be removed, for example unscrewed, for the cleaning process, so that the actual radiation tube, i.e. the guide chamber with the outlet window, is now exposed.

In the case of a further advantageous method the outlet window is acted upon with at least two different flowable media or is subjected to two media respectively for its cleaning. It is advantageous for the outlet window to be acted upon with at least three different media, and in a particularly preferred manner, with at least four different media, for its cleaning.

In the case of a further advantageous method the outlet window is dipped into a bath of liquid for its cleaning. It is advantageous for this to be a bath of the cleaning liquid. It is advantageous for the aforesaid outlet windows to have a thickness in the region of 10 μm. There is therefore a risk in the case of a mechanical cleaning in some form that the aforesaid titanium foil will be damaged or pierced respectively as a result of this. A chemical cleaning is thus proposed in which the titanium foil or the external surface thereof respectively is dipped into a chemical cleaning agent.

In the case of a further advantageous method at least one cleaning medium is an acid. In the case of a further preferred method at least one cleaning medium is a lye.

In this way, it is possible for example for the outlet window first to be acted upon with an acid, then with water, in particular with distilled water, then with a lye and finally once again with water, and in particular with sterilized water.

For a complete cleaning procedure it is proposed that the radiation device should first be switched off, then the cooling air should be switched off, and in a further step the aforesaid cooling tube or the further element respectively should be removed, and in addition the stressing—as described above—with the different media should be carried out and in a further step the cooling tube can be mounted again and in a further step the cooling air should first be switched on. After that there is a wait of a pre-set duration and finally the preparation of the production or the preparation of the sterilization respectively for containers can be started again.

In the case of a further advantageous method the outlet window is acted upon by at least one cleaning medium for a period of time which is greater than 5 minutes. It is preferable for the period of time to be greater than 10 minutes, preferably greater than 20 minutes, preferably greater than 30 minutes, in a particularly preferred manner greater than 40 minutes, and in a particularly preferred manner greater than 50 minutes. It is preferable for the outlet window to be acted upon by a plurality of cleaning media and in a particularly preferred manner by all the cleaning media for a period of time which is greater than 5 minutes, preferably greater than 10 minutes, preferably greater than 20 minutes, preferably greater than 30 minutes, in a particularly preferred manner greater than 40 minutes, and in a particularly preferred manner greater than 50 minutes.

The Applicants have discovered that for a particularly efficient cleaning of the outlet window the latter should be subjected to the respective cleaning substances over a prolonged period of time.

In the case of a further advantageous method the outlet window is introduced into a container which contains the cleaning medium. In this way, an efficient cleaning of the external surface can be achieved in a particularly simple manner. It is advantageous for this container to be the same type of container which is also sterilized by the plant. In this case it would be possible for the rod-like body or the outlet window respectively to be actively moved and to be introduced into the container. It would also, however, be possible—and this is preferred—for the container to be moved and to be folded over the outlet window to some degree.

In the case of a further advantageous method a gas present at the outlet window is removed before or during the cleaning operation. An air bubble can form on the outlet window during the immersion of the latter. In this case it should be taken into consideration that the outlet window can preferably be set back slightly with respect to a housing carrying the latter. In this way, the aforesaid gas bubble or air bubble respectively can be formed during the immersion. This removal of the aforesaid air bubble is preferably carried out by the outlet window or the aforesaid radiation finger respectively being set in motion at least for a short time, for example by being touched by a finger.

As mentioned above, the individual cleaning media act over prolonged periods of time, for example between one and six hours. It is also possible, however, for the exposure time to vary individually for separate cleaning media.

It was possible for the influence of the cleaning to be verified with reference to an increase in the emission flow.

It is advantageous for both an external treatment and an internal treatment to be carried out within the framework of a sterilization procedure of the plastics material containers. In this case it is advantageous for the plastics material container to be disinfected from the outside by way of a stationary radiation device, and in particular a stationary panel radiator, within the framework of the external treatment. It is preferable for finger radiators to be used in the internal treatment, as mentioned above. These are advantageously arranged on a rotating turntable and the plastics material containers to be sterilized are advantageously moved over the aforesaid radiation fingers or even the outlet window thereof respectively during the rotation of this turntable. In this case the two radiation devices imitate electrons which disinfect the irradiated surfaces.

It is pointed out that the possibility of cleaning proposed here is also possible for the aforesaid panel radiators. In this case the outlet windows can likewise be acted upon with a cleaning medium, and in particular a liquid cleaning medium. In this case, however, it is not necessary for the outlet windows to be introduced into the plastics material containers during the sterilization of the latter. The Applicants reserve the right to claim the present cleaning method in general also for other electron radiators. The method is suitable in particular for the aforesaid radiator fingers, however, since the latter have a particularly sensitive outlet window.

By means of the method described here it is possible for the service life, in particular of these finger radiators, to be increased. In order to prevent the outlet windows or the window foil respectively of a radiator of this type from being severed, it is proposed, as mentioned above, for this outlet window or the foil respectively to be cleaned at regular intervals. In this case, as mentioned above, it is preferable for containers to be provided which are filled with a cleaning agent such as for example hydrochloric acid and/or lye and which are moved over the windows to be cleaned. In this case it would also be possible, in particular in a manner dependent upon a degree of contamination, to repeat the respective cleaning procedures.

By means of a regular cleaning, in particular of the aforesaid outlet windows or foils respectively, the service life of a radiator of this type is increased dramatically. In addition, the costs can be kept low on account of a minimal use of chemicals. This minimal use of chemicals can be achieved inter alia in that the aforesaid radiation fingers are dipped into those containers which according to the type are also used for sterilization, in particular plastics material pre-forms. The advantage lies in the fact that the already existing apparatus can also be used for the cleaning operation, in that the outlet windows are moved into the plastics material pre-forms (as also in the cleaning operation). In addition, the internal volume of these plastics material pre-forms is very small, so that cleaning agents also have to be used in only small quantities. In this case it is advantageous for those elements which are used for the working operation to be used also for the cleaning operation.

The present invention further relates to an apparatus for the sterilization of plastics material containers. This apparatus has in this case a charge carrier product device which generates charge carriers and, in particular, electrons. In addition, the apparatus has a guide chamber for guiding the charge carriers generated by the charge carrier product device as well as an outlet window through which the charge carriers can emerge out of the guide chamber. It is preferable in this case for that region through which the charge carriers are conveyed or preferably accelerated respectively also to be set under a (partial) vacuum.

It is advantageous for the aforesaid outlet window to be capable of being introduced into the plastics material container to be sterilized through an aperture of this plastics material container.

According to the invention the apparatus has a cleaning device which acts upon the outlet window with a liquid cleaning medium at least for a time. It is advantageous in this case for this cleaning device to be designed in such a way that the outlet window can be dipped into the cleaning medium.

It is advantageous for this cleaning device to have a moving device which introduces the outlet windows into the cleaning medium.

In the case of a further advantageous embodiment the apparatus has a cooling device which cools the aforesaid outlet window at least in one working operation, in particular in that this cooling device acts upon the outlet window with a gaseous medium.

In the case of a further advantageous embodiment this cooling device has a second housing which is preferably formed around the guide chamber at least in part in a peripheral direction. It is advantageous in this case for a channel, through which the gaseous medium can be conveyed, to be formed between this second housing and the guide chamber. This channel is preferably likewise filled with cleaning medium and it preferably permits an alternative supply of cleaning medium to the location of the cleaning.

In the case of a preferred embodiment the apparatus has a plurality of sterilization devices, for example an external sterilization device which is intended to irradiate an external surface of the plastics material pre-forms with the electrons, and an internal irradiation device which is intended to act upon an internal surface of the plastics material pre-forms with the electrons. In addition, a plurality of conveying device can be provided which convey the plastics material pre-forms during the sterilization thereof, such as for example conveying star wheels which convey the plastics material pre-forms from a first sterilization device to a second sterilization device.

It is preferable for at least one conveying device, which conveys or transports respectively the plastics material pre-forms from a first sterilization device (in particular an external sterilization device) to a second sterilization device (in particular an internal sterilization device), to be designed in the form of a distribution star wheel which is capable not only of conveying the plastics material containers but also of changing a distribution or an interval respectively of two successive plastics material containers.

A distribution delay star wheel of this type can have in this case a movable, and in particular rotatable, carrier on which gripping elements for gripping the plastics material containers are arranged in turn so as to be pivotable and/or radially movable. It is preferable for first an external sterilization device for sterilizing an external surface of the plastics material pre-form and then an internal sterilization device for sterilizing an internal surface to be provided in a conveying direction of the plastics material pre-forms.

In the case of a further advantageous embodiment the aforesaid second housing is capable of being removed from the guide chamber. In this way, for example, the second housing can be screwed onto the guide chamber.

In the case of an advantageous embodiment the cleaning agent can be received (in particular during the cleaning procedure) in a plastics material container. It is preferable for this to be a plastics material container which in terms of its category corresponds to those plastics material containers which are to be sterilized. In the case of a further advantageous embodiment the cleaning device has a container into which the outlet window is capable of being introduced. It is advantageous in this case for the container to be in terms of its type the same container which is also sterilized. In particular, the container is a plastics material pre-form.

In the case of a further advantageous embodiment the guide chamber has a rod-like body, or forms a rod-like body respectively, which is capable of being introduced into the plastics material pre-form.

In the case of a further advantageous embodiment the apparatus has a carrier on which a plurality of the apparatus described above, and in particular a plurality of the radiators described above, are arranged. It is advantageous for this to be a rotatable carrier.

In the case of a further advantageous embodiment the apparatus has a drive device which allows the rod-like bodies or the outlet windows respectively to be introduced in a working operation into the plastics material containers to be sterilized.

In the case of a further advantageous embodiment the outlet window has a foil or is designed in the form of a foil respectively. It is particularly preferred for this to be a titanium foil. It is preferable for this foil to have a thickness which is between 6 and 20 µm, preferably between 8 and 15 µm, and in a particularly preferred manner between 8 and 12 µm.

In the case of a further advantageous embodiment the apparatus has a filling device which fills those containers—into which the outlet windows are dipped—at least in part with a cleaning medium.

In addition, the cleaning device can preferably have storage containers or storage devices respectively which store the aforesaid cleaning media.

In this way, it is possible for example for the aforesaid cleaning operation also to be capable of being carried out automatically. In this case it is possible for the individual containers first to be filled with one or more cleaning liquids in a preparatory stage of the cleaning operation. After that, the radiation fingers can dip into these containers. In this case it would be possible within the framework of the cleaning operation for a plurality of the aforesaid containers to be filled with a first cleaning medium and then for the outlet windows to be dipped into these containers for a pre-set period of time. After that, the containers can be emptied and filled with a second cleaning liquid and the outlet windows can be dipped in again here.

In this way, it is possible for the cleaning operation to be carried out automatically.

BRIEF DESCRIPTION OF THE DRAWINGS

Further advantages and embodiments are evident from the accompanying drawing. In the drawing

DETAILED DESCRIPTION OF THE INVENTION

Figure 1:
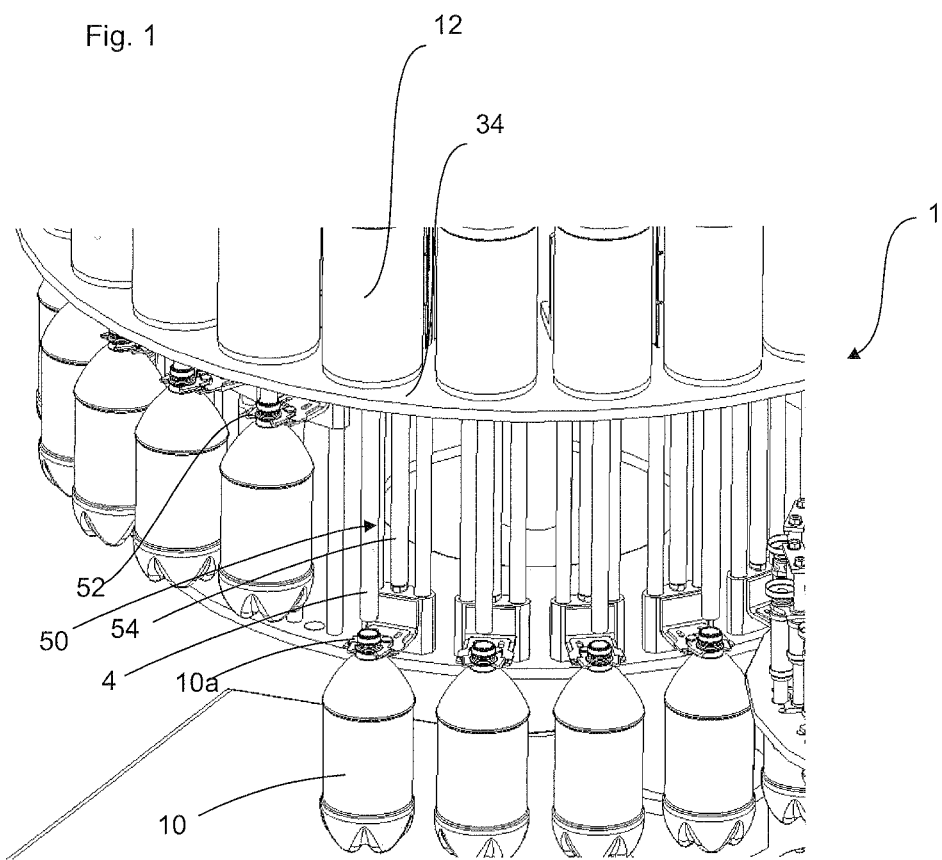
FIG. 1 is an illustration of an apparatus according to the invention.

FIG. 1 is an illustration of an apparatus according to the invention for the sterilization of containers. In this case this apparatus has a rotatable carrier 34 on which a plurality of apparatus 1 for the sterilization of plastics material containers 10 are arranged. The containers 10 are in this case plastic bottles, but it should be pointed out that plastics material pre-forms can also be sterilized with the apparatus according to the invention and this is also preferred.

The reference number 50 designates in its entirety a moving device which in this case moves, and in particular raises, the plastics material containers 10, and, in this way, introduces the individual radiation fingers 4 into the containers 10 by way of the apertures of the latter. The moving devices 50 have in each case holding devices 52 which hold the containers, and in this case in particular hold them below the carrying ring thereof. In addition, the moving devices 50 have a rod body 54 which can be moved in a linear manner along the longitudinal direction thereof in order to raise the containers.

In addition, the apparatus preferably also has a clean room, inside which the plastics material pre-forms are conveyed during the working operation. This clean room can be bounded in this case by a plurality of walls (not shown), it being preferable for one of these walls to be movable with respect to a further wall.

Figure 2:
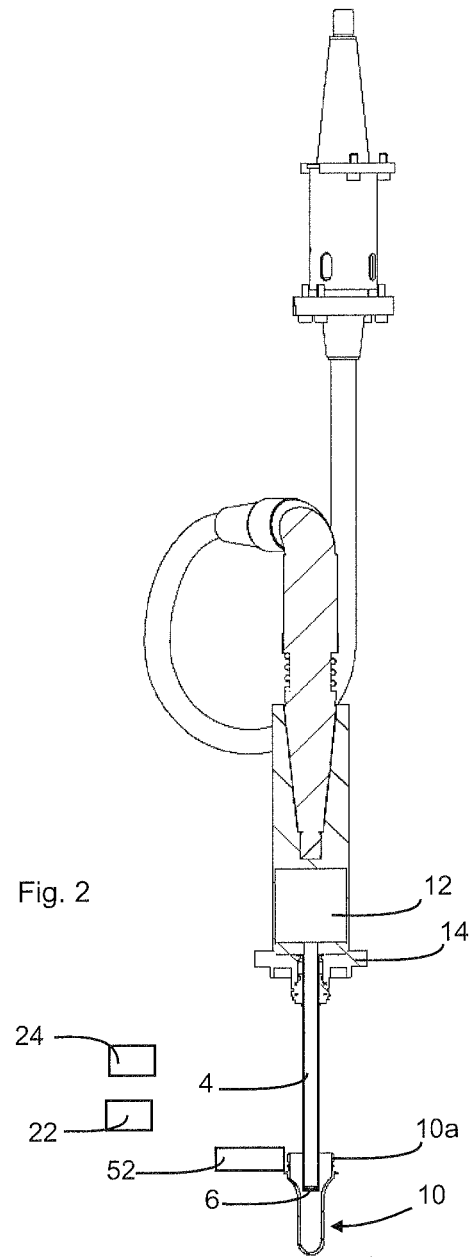
FIG. 2 is an illustration of an apparatus according to the invention in a cleaning mode.

FIG. 2 is a detailed view of an apparatus according to the invention in a cleaning mode. In this case the reference number 12 refers to an acceleration chamber in which the electrons are accelerated. This acceleration chamber is not introduced in this case [into] the containers. This acceleration chamber 12 is adjoined by a chamber 4 for example in the form of a finger which is capable of being introduced into the plastics material containers 10 by way of the aperture 10a thereof. The outlet window 6, by way of which the electrons can emerge from the chamber 4, is provided at the lower end of this radiation finger.

The reference number 22 designates roughly diagrammatically a drive device which for cleaning purposes raises the container 10 upwards in this case and, in this way, introduces the outlet window into the plastics material pre-form 10. This can be in this case the same drive device which also raises and lowers the plastics material pre-forms in working operation.

The reference number 24 designates a control device which controls the movement of the plastics material pre-forms 10 in the cleaning mode. In this case it is possible for the plastics material pre-forms 10 to be raised and, in this way, for the chamber 4 with the outlet window 6 to be dipped in the plastics material pre-forms. After that, the apparatus can be held for a prolonged period of time in this state, in order—as described above—to carry out the cleaning of the outlet window 6.

In this case it is possible for this procedure to be carried out at the same time with all the radiation devices 1 which are arranged on the common carrier 34. In a further step, as described above, other cleaning media can be used.

The Applicants reserve the right to claim all the features disclosed in the application documents as being essential to the invention, insofar as they are novel either individually or in combination as compared with the prior art.

LIST OF REFERENCES 1 apparatus for the sterilization of containers
2 charge carrier generation device
4 chamber
6 outlet window
10 plastics material containers, container, plastics material pre-form
10a aperture
12 acceleration chamber
20 cleaning device
22 drive device
24 control device
34 carrier
50 moving device
52 holding device
54 rod body

The invention claimed is:

1. A method of operating an apparatus for the sterilization of plastics material containers comprising:
generating charge carriers in a working operation and conveying the charge carriers through a guide chamber to emerge from the guide chamber through an outlet window bounding the guide chamber;
introducing the outlet window into the plastics material containers at least in part through an aperture of the aforesaid plastics material containers during sterilization of the plastics material containers; and
cleaning the outlet window with a flowable cleaning medium in a cleaning operation of the apparatus by introducing the outlet window into a container which contains the cleaning medium.

2. The method according to claim 1, comprising:
acting upon the outlet window with a liquid cleaning medium employed in the cleaning operation of the apparatus.

3. The method according to claim 1, comprising:
cooling the outlet window at least for a time by action of a gaseous medium during the working operation.

4. The method according to claim 1, comprising:
removing at least one element of a device for cooling the outlet window from the guide chamber before commencing the cleaning operation.

5. The method according to claim 1, comprising:
acting upon the outlet window with at least two different flowable media for the cleaning thereof.

6. The method according to claim 1, wherein the outlet window is dipped into a bath of liquid for cleaning.

7. The method according to claim 1, wherein the at least one cleaning medium comprises an acid.

8. The method according to claim 1, wherein the at least one cleaning medium comprises a lye.

9. The method according to claim 1, wherein:
the outlet window is acted upon by at least one cleaning medium for a period of time which is greater than 5 minutes.

10. The method according to claim 1, further comprising:
removing gas present at the outlet window before or during the cleaning operation.

11. The method according to claim 2, comprising:
cooling the outlet window at least for a time by action of a gaseous medium during the working operation.

12. The method according to claim 2, wherein the outlet window is dipped into a bath of liquid for cleaning.

13. The method according to claim 2, wherein at least one cleaning medium comprises an acid.

14. The method according to claim 2, wherein at least one cleaning medium comprises a lye.

15. The method according to claim 2, wherein the outlet window is acted upon by at least one cleaning medium for a period of time which is greater than 5 minutes.

16. The method according to claim 1, comprising:
    cleaning the outlet window at times other than during the working operation.

17. The method according to claim 1, wherein the cleaning medium is of a type used to sterilize plastics material containers.

18. The method according to claim 1, comprising:
    filling those containers, into which the outlet windows are dipped, at least in part, with a cleaning medium by a filling device.

19. The method according to claim 1, further comprising the steps in sequence of:
    filling the plurality of containers, into which the outlet windows are to be dipped, at least in part, with a first cleaning medium;
    dipping the outlet windows into the containers for a pre-set period of time;
    emptying the containers;
    refilling the containers at least in part with a second cleaning liquid; and
    again dipping the outlet windows into the containers.

* * * * *